US00PP36785P2

(12) United States Plant Patent
Jackson et al.

(10) Patent No.: US PP36,785 P2
(45) Date of Patent: Jul. 1, 2025

(54) ***CERCIS* PLANT NAMED 'JN100'**

(50) Latin Name: *Cercis canadensis*
Varietal Denomination: JN100

(71) Applicants: Ray Jackson, Belvidere, TN (US); Cindy Jackson, Belvidere, TN (US)

(72) Inventors: Ray Jackson, Belvidere, TN (US); Cindy Jackson, Belvidere, TN (US)

(73) Assignee: GREENLEAF NURSERY CO., Park Hill, OK (US)

( * ) Notice: Subject to any disclaimer, the term of this patent is extended or adjusted under 35 U.S.C. 154(b) by 0 days.

(21) Appl. No.: 18/799,941

(22) Filed: Aug. 9, 2024

(51) Int. Cl.
*A01H 5/02* (2018.01)
*A01H 6/54* (2018.01)

(52) U.S. Cl.
USPC ..... Plt./216
CPC ..... *A01H 6/54* (2018.05)

(58) Field of Classification Search
USPC ..... Plt./216
CPC ..... A01H 6/54; A01H 5/02
See application file for complete search history.

(56) References Cited

PUBLICATIONS

Garden Debut New Varieties Catalog, Jul. 19, 2023, p. 14 (Year: 2023).*

* cited by examiner

*Primary Examiner* — Keith O. Robinson
(74) *Attorney, Agent, or Firm* — Penny J. Aguirre

(57) ABSTRACT

A new cultivar of *Cercis canadensis* tree named 'JN100' that is characterized by its unique foliage colors; bright red and orange emerging foliage that changes to green when the leaves mature, its emerging foliage color holds for a long time period, its upright plant habit, its foliage that is resistant to leaf scorch in mid-summer in Southern climates, and its slow growth rate with reduced branch damage due to wind and ice.

2 Drawing Sheets

Botanical classification: *Cercis canadensis.*
Variety denomination: 'JN100'.

CROSS-REFERENCE TO RELATED APPLICATIONS

This application is co-pending with U.S. Plant Patent Applications filed for plants derived from the same breeding program that are entitled *Cercis* Tree Named 'JN104' (U.S. Plant patent application Ser. No. 18/799,948), *Cercis* Tree Named 'JN106' (U.S. Plant patent application Ser. No. 18/799,953), and *Cercis* Tree Named 'JN31' (U.S. Plant patent application Ser. No. 18/799,927).

BACKGROUND OF THE INVENTION

The present invention relates to a new and distinct cultivar of *Cercis canadensis* and will be referred to hereafter by its cultivar name, 'JN100'. 'JN100' is an Eastern redbud tree grown for use as a landscape plant.

The new *Cercis* was selected by the Inventors in summer of 2019 in a cultivated field in Belvidere, Tennessee. The field had been planted with seeds collected in 2016 and pooled from *Cercis canadensis* cultivars 'JN2' (U.S. Plant Pat. No. 21,451) and 'Ruby Falls' (U.S. Plant Pat. No. 22,097). As the two cultivars were the only cultivars growing in the area of seed collection, they are presumed to be the parent plants, however it is unknown which plants are the male or female parent.

Asexual propagation of the new cultivar was first accomplished by budding onto seedling understock of *Cercis*

*canadensis* (Not Patented) by one of the Inventors in August of 2019 in Belvidere, Tennessee. Asexual propagation by budding has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'JN100' as a unique cultivar of *Cercis*.

1. 'JN100' exhibits unique foliage colors; bright red and orange emerging foliage that changes to green when the leaves mature.
2. 'JN100' exhibits emerging foliage color holds for a long time period.
3. 'JN100' exhibits an upright plant habit.
4. 'JN100' exhibits foliage that is resistant to leaf scorch in mid-summer in Southern climates.
5. 'JN100' exhibits a slow growth rate with reduced branch damage due to wind and ice.

The probable parent plant, 'JN2', differs from 'JN100' in having yellow and tangerine emerging foliage and a faster growth habit with a greater susceptibility to wind and ice damage. 'Ruby Falls' differs 'JN100' in having purple emerging foliage and a weeping plant habit. 'JN100' can be compared to the *Cercis canadensis* cultivar 'NC2016-2' (U.S. Plant Pat. No. 31,260). 'NC2016-2' is similar to 'JN100' in having foliage that emerges bright red and orange in color. 'NC2016-2' differs from 'JN100' in having emerging foliage that is duller red in color and changes to yellow in color and in having a less upright plant habit with drooping branches.

'JN100' can also be compared to the co-pending cultivars of *Cercis canadensis* 'JN104', 'JN106', and 'JN31'. 'JN104' differs from 'JN100' in having dark green foliage and a weeping plant habit. 'JN106' differs from 'JN104' in having foliage that emerges burgundy purple that changes to dark green in color. 'JN31' differs from 'JN100' in having emerging foliage that is yellow in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Website listings include but may not be limited to listings by Piedmont Carolina Nursery, Jackson and Perkins, Territorial Seed (Territ), Mr. Maple, ServeScape, Spring Hill Nursery, Garden Debut, Glass Farm Nursery, Fast Growing Trees, Covingtons, Wayside Gardens, Park Seed, Bonsaitreepromo, New Blooms Nursery, and Sooner Plant Farm.

BRIEF DESCRIPTION OF THE DRAWINGS

The accompanying color photographs illustrate the overall appearance and distinct characteristics of the new *Cercis*. The photographs were taken of a 3-year-old plant of the new cultivar as grown in a 5-gallon container in Belvidere, Tennessee.

The photograph in FIG. 1 provides a view of trees of 'JN100'.

Figure 1:
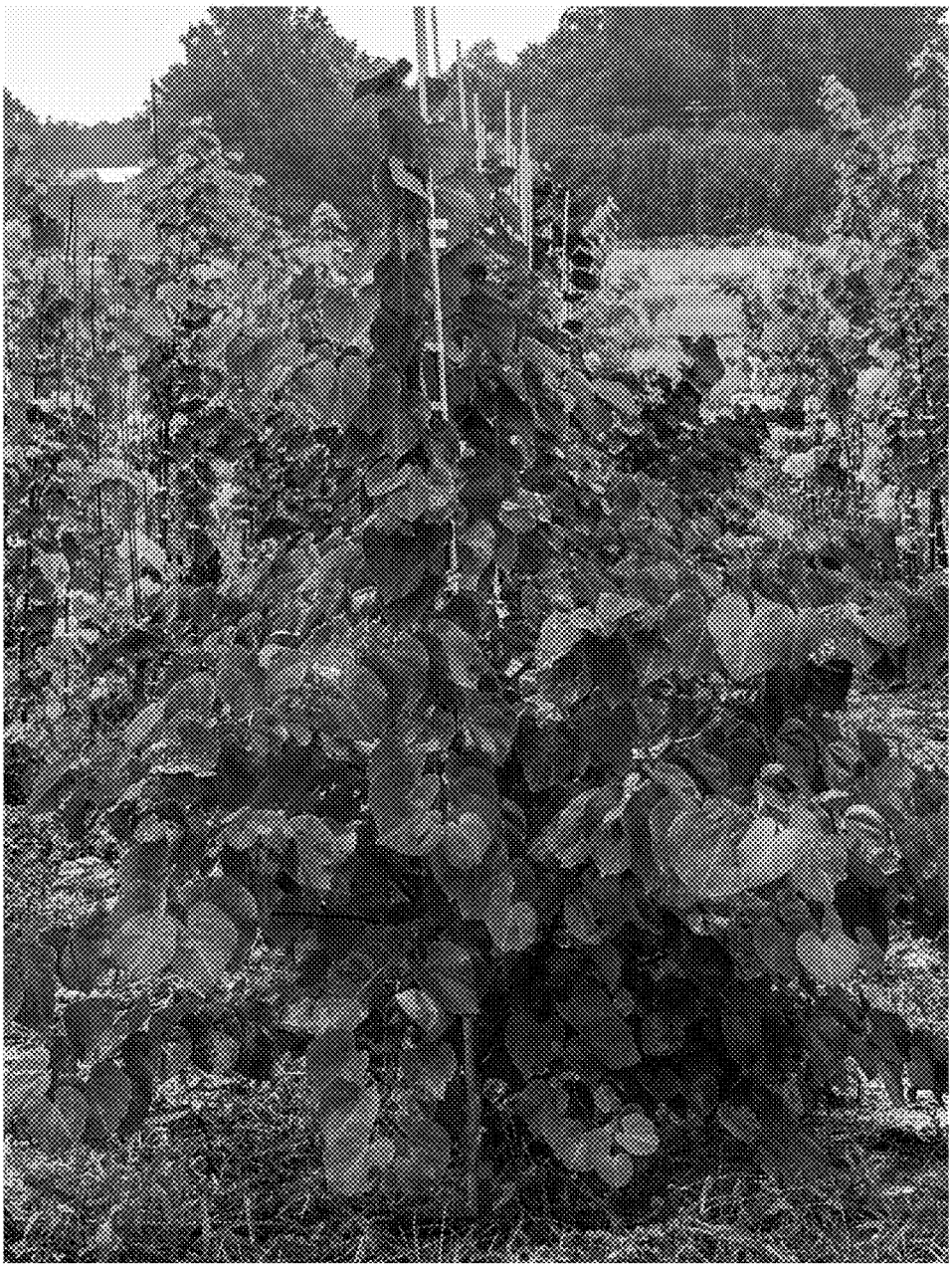
Figure 2:
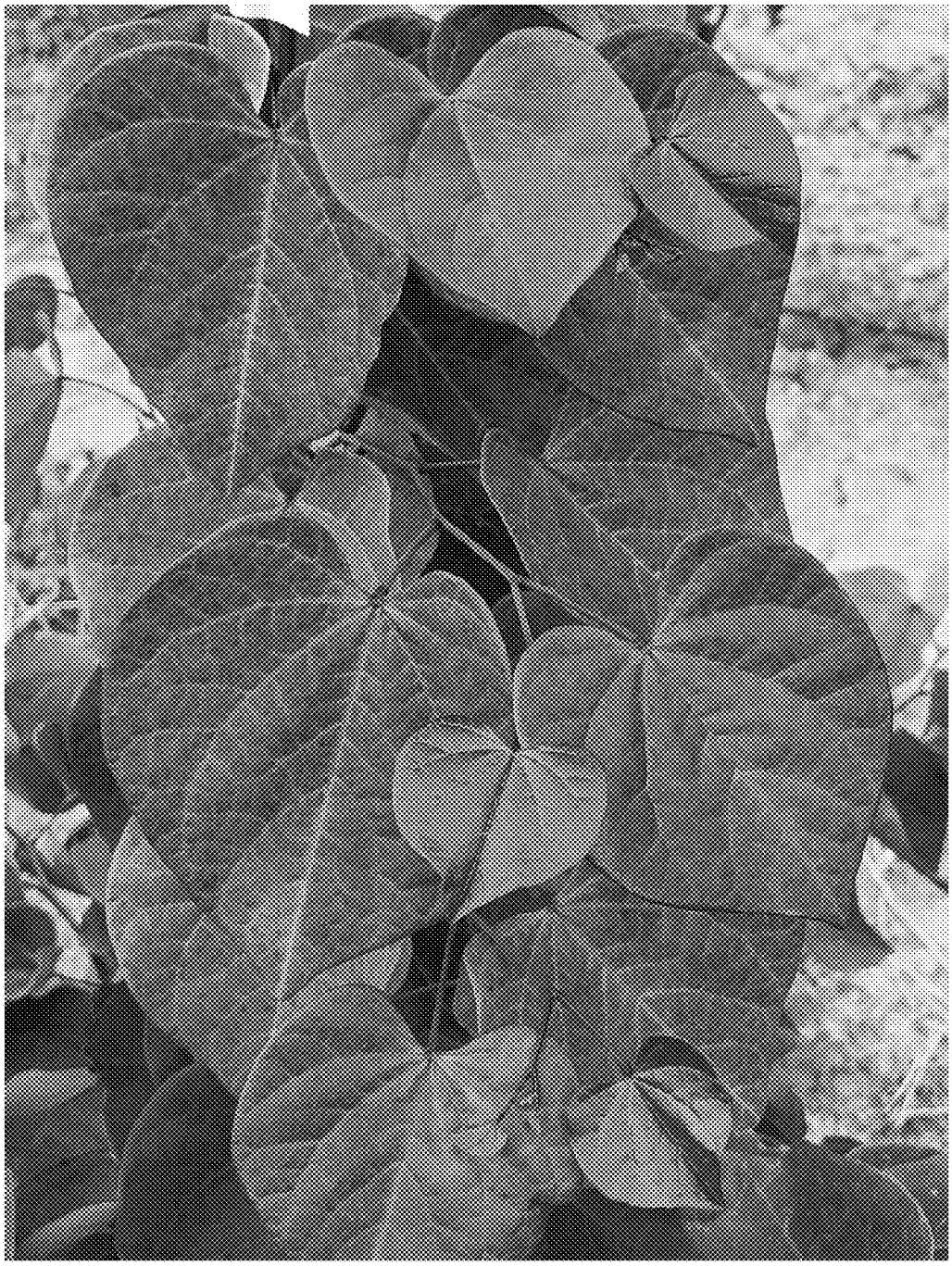

The photograph in FIG. 2 provides a close-up view of the new foliage of 'JN100'.

The colors in the photographs are as close as possible with the digital photography techniques available, the color values cited in the detailed botanical description accurately describe the colors of the new *Cercis*.

DETAILED BOTANICAL DESCRIPTION

The following is a detailed description of 3-year-old plants of the new cultivar as grown in a 5-gallon container in Belvidere, Tennessee. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—3 to 4 weeks in early spring in Belvidere, Tennessee.

*Plant type.*—Deciduous tree.

*Plant habit.*—Upright and densely branched.

*Height and spread.*—Average of 97 cm in height and 42 cm in width as grown in a container, as a mature tree reaches about 3 m in height and 4.5 m in spread in the landscape.

*Cold hardiness.*—At least to U.S.D.A. Zone 5.

*Environmental factors.*—Resistant to winter and ice damage and sun scorch when grown in Southern climates.

*Diseases and pests.*—No susceptibility or resistance to diseases or pests has been observed.

*Root description.*—Fibrous, 200A in color.

*Propagation.*—Budding.

*Propagation timing.*—Budding in July-August, growth begins in the spring and takes 7 months to become a salable whip.

*Growth rate.*—Moderate.

Branch description:

*Branch shape.*—Rounded, slightly zig-zag growth habit.

*Branch color.*—New growth; N144A, mature branches; N200B to N200C, flushed with N200A, moderately covered with lenticels 155A in color, mature bark; 202A and 202B, very densely covered with lenticels 161A in color.

*Branch size.*—Trunk; 3.5 cm in width, 4 cm in length, main branch; 80 cm in height, 1.8 cm in diameter, lateral branches; an average of 24 cm in length and 8 mm in diameter (branches were cut back), new growth; 7 mm in length, 2 mm in diameter.

*Branch surface.*—Young branches; glabrous, semi-glossy, mature bark; glabrous, matte, lustrous, relatively smooth, and moderately lenticellate.

*Internode length.*—An average of 2.5 cm.

*Branching habit.*—An average of 6 lateral branches per main branch, 4 branches per lateral branch.

Foliage description:

*Leaf shape.*—Reniform.

*Leaf division.*—Simple.

*Leaf base.*—Cordate.

*Leaf apex.*—Ovate.

*Leaf fragrance.*—None.

*Leaf venation.*—Palmate, color; young upper surface 147C and lower surface 178A, color: young; upper and lower surface 167B, mature upper and lower surface 39A.

*Leaf margins.*—Entire.

*Leaf arrangement.*—Alternate.

*Leaf aspect.*—Held reflexed downward from petiole (hanging) to outward.

*Leaf attachment.*—Petiolate.

*Leaf number.*—An average of 25 leaves per lateral stem.

*Leaf surface.*—New and mature leaf upper surface; smooth, glabrous, satiny and slightly glossy, new and mature leaf lower surface; smooth, glabrous, satiny and matte.

*Leaf size.*—An average of 8 cm in length and width.

*Leaf color.*—Emerging; both surfaces 178A, changing to a color between NN137A and 138A and suffused on lower surface with 178A, young; upper and lower surface a blend of N170A, 171A, flushed with 45A and 187B, mature leaf upper and lower surface; a blend of 45B and 46D, fall; 162A on both surfaces.

*Petiole.*—An average of 3 cm in length and 1.5 mm in width, slightly glossy surface, flexible and moderately strong, color; young 145A, flushed with N170A and 171A, mature 46A.

*Internode length.*—Average of 3 cm.

Inflorescence description:

*Inflorescence type*.—Cauliflorous clusters of papilionaceous (pea-like) flowers.

*Inflorescence size*.—Up to 3 cm in width and 1.9 cm in depth.

*Lastingness of inflorescence*.—2 to 3 weeks.

*Flower size*.—An average of 1 cm in length and 9 mm in width.

*Flower fragrance*.—Moderate, sweet floral scent.

*Flower number*.—An average of 5 flowers per cluster.

*Bracts*.—Average of 7, surrounding base of inflorescence, whorled, imbricate, ovate in shape, acute apex, an average of 1 mm in length and width, color; N200A, glabrous and matte surface.

*Peduncles*.—An average of 1 cm in length and 0.5 mm in diameter, color; 187C, base 187A, glabrous and matte surface, moderately strong, slightly curved to straight, held at all directions from branch node in a whorled arrangement.

*Pedicels*.—None, peduncles attached in cluster at branch.

*Flower buds*.—Slightly curved, beak-shaped, 5 mm in length, 2 mm in width, glabrous and matte surfaces, color; NN78A, veins N80C.

*Flower type*.—Papilionaceous.

*Calyx*.—Campanulate in shape, 4 mm in length, 3 mm in diameter.

*Sepals*.—5, fused, upper 5% of tip free, apex acute, 3 mm in length, free portion 0.5 mm in length, 0.8 mm in width, entire margins, both surfaces are glabrous and matte and 187A in color.

*Corolla features*.—Papilionaceous, bilateral with two upper petals around the stamens and pistil, a center petal, and two lower petals under the center petal, upper petals; obovate and cup shaped, margins slightly undulate, average of 8 mm in length, 5 mm in width, both surfaces glabrous, slightly glossy, color when opening and fully open; 72A, top 71A, base 76A, center petal; 2 mm in length, 3 mm in width, both surfaces glabrous, slightly glossy, broad in shape and curled downward, rounded apex, cuneate base, entire margins, slightly undulate, color when opening and fully open; a blend of 72A and 76A, veins 71A, lower petals; elliptical in shape, curled downward, margins moderately undulate, average of 7 mm in length, 3 mm in width, both surfaces glabrous, slightly glossy and slightly transparent at the base, color when opening and fully open; top to mid-section 72A, base and veins 76A.

Reproductive organs:

*Gynoecium*.—Pistil; 1, stigma; minute, indistinguishable, style; an average of 6 mm in length, 1 mm in width, 71A in color, ovary; round, in bottom of calyx, 187A in color.

*Androecium*.—Stamens; 10, anthers; club to oval shaped, an average of 0.4 mm in diameter, 200A in color, filament; an average of 5 mm in length and 0.5 mm in width, color; top 68C, mid-section 72C, base 71A, glossy and transparent surface, pollen is abundant in quantity, 11B in color.

*Seed and fruit*.—None observed to date.

It is claimed:

1. A new and distinct cultivar of *Cercis canadensis* tree named 'JN100' as herein illustrated and described.

* * * * *